United States Patent [19]
Faries, Jr. et al.

[11] Patent Number: 5,400,616
[45] Date of Patent: Mar. 28, 1995

[54] METHOD AND APPARATUS FOR FORMING AND COLLECTING SURGICAL SLUSH

[75] Inventors: Durward I. Faries, Jr., McLean, Va.; Bruce R. Heymann, Silver Spring, Md.; Mark Licata, Richmond, Va.

[73] Assignee: O.R. Solutions, Inc., Reston, Va.

[21] Appl. No.: 274,869

[22] Filed: Jul. 14, 1994

Related U.S. Application Data

[62] Division of Ser. No. 125,279, Sep. 23, 1993, Pat. No. 5,331,820.

[51] Int. Cl.⁶ ............................................. F25C 1/00
[52] U.S. Cl. .................................... 62/340; 62/342
[58] Field of Search .............. 62/66, 68, 340, 342; 128/846, 849; 4/DIG. 18, 452, 484, 580, 655

[56] References Cited

U.S. PATENT DOCUMENTS

| | | | |
|---|---|---|---|
| 4,393,659 | 7/1983 | Keyes et al. | 62/66 |
| 4,934,152 | 6/1990 | Templeton | 62/66 |
| 5,163,299 | 11/1992 | Faries, Jr. et al. | 62/66 |
| 5,174,306 | 12/1992 | Marshall | 128/849 |

Primary Examiner—William E. Tapoical

[57] ABSTRACT

Frozen pieces of sterile medium, such as saline, are dislodged from a sterile drape container in a surgical slush producing machine a manipulating the drape relative to the cooled basin to which the drape container conforms. Manipulation of the drape is achieved by pushing, twisting, pulling, lifting, etc., on the drape to displace it from the basin. Such movement of the drape may be effected on a continuous and automatic basis, or by manual means using a member or implement to facilitate drape movement. The system cabinet includes a refrigerated compartment for pre-chilling sterile liquid to be used in forming the surgical slush.

27 Claims, 9 Drawing Sheets

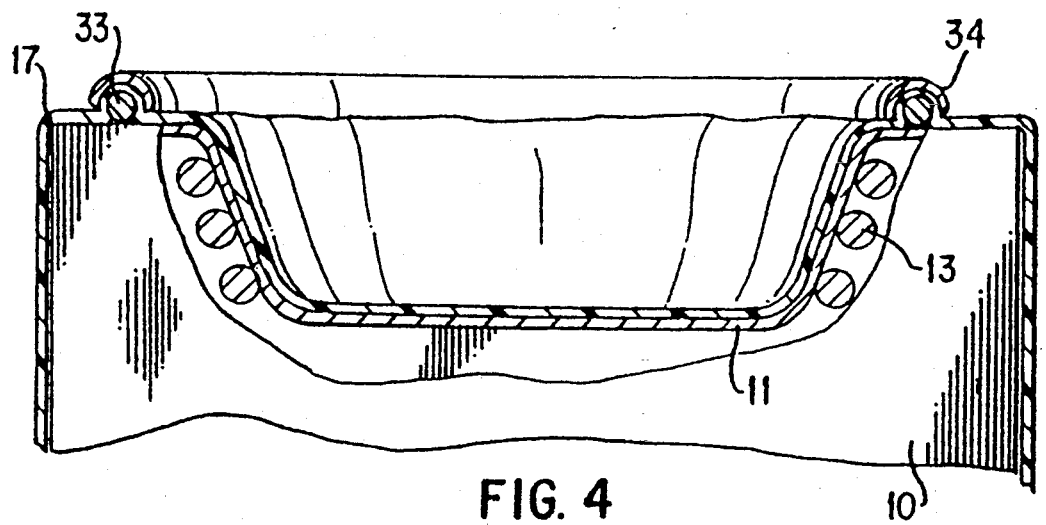
FIG. 4
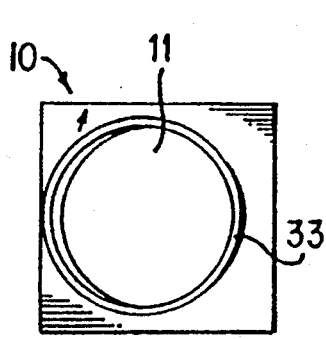 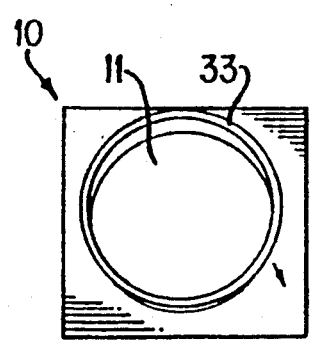 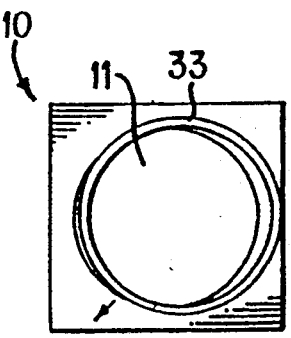
FIG. 5  FIG. 6  FIG. 7
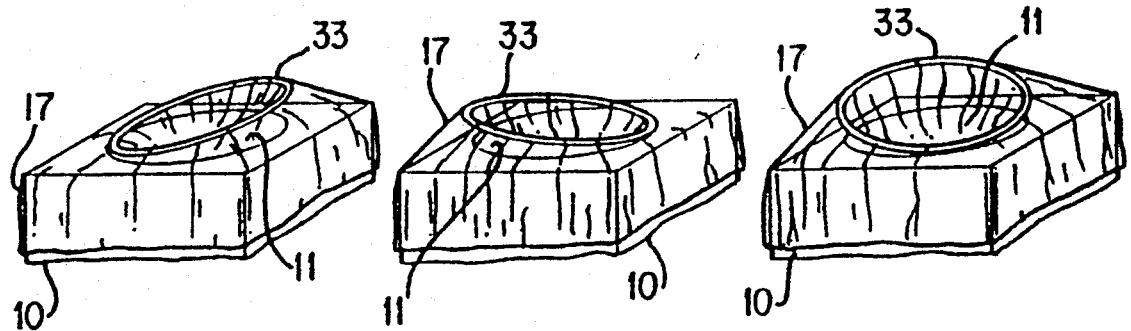
FIG. 8  FIG. 9  FIG. 10

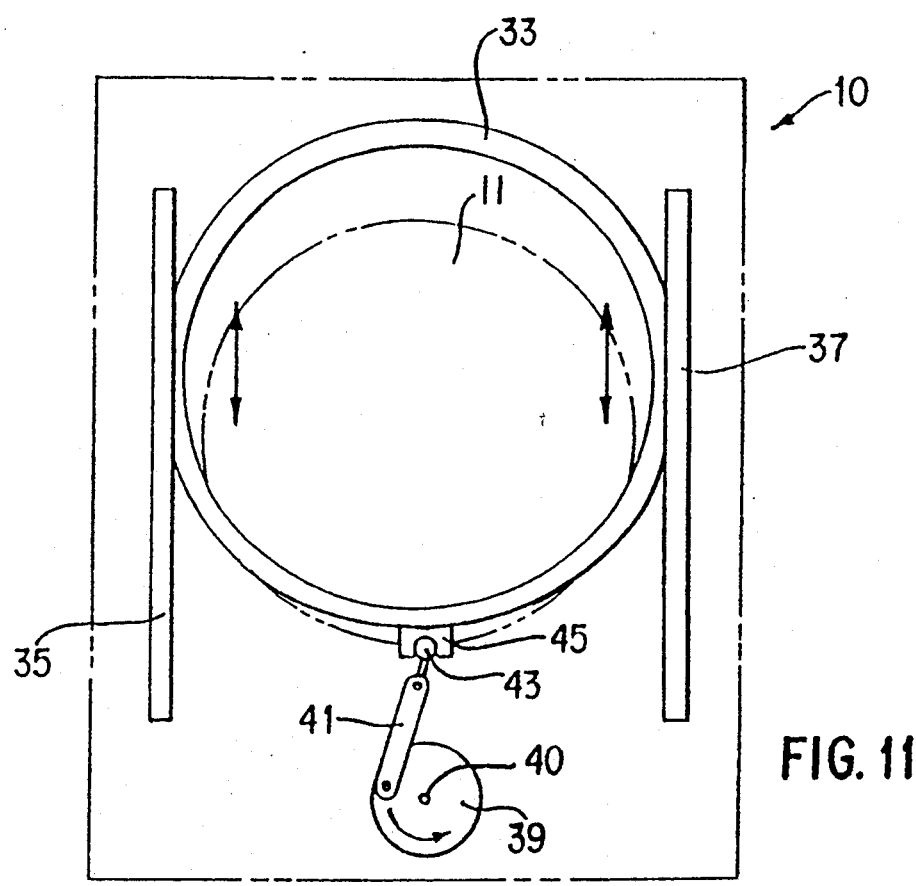
FIG. 11
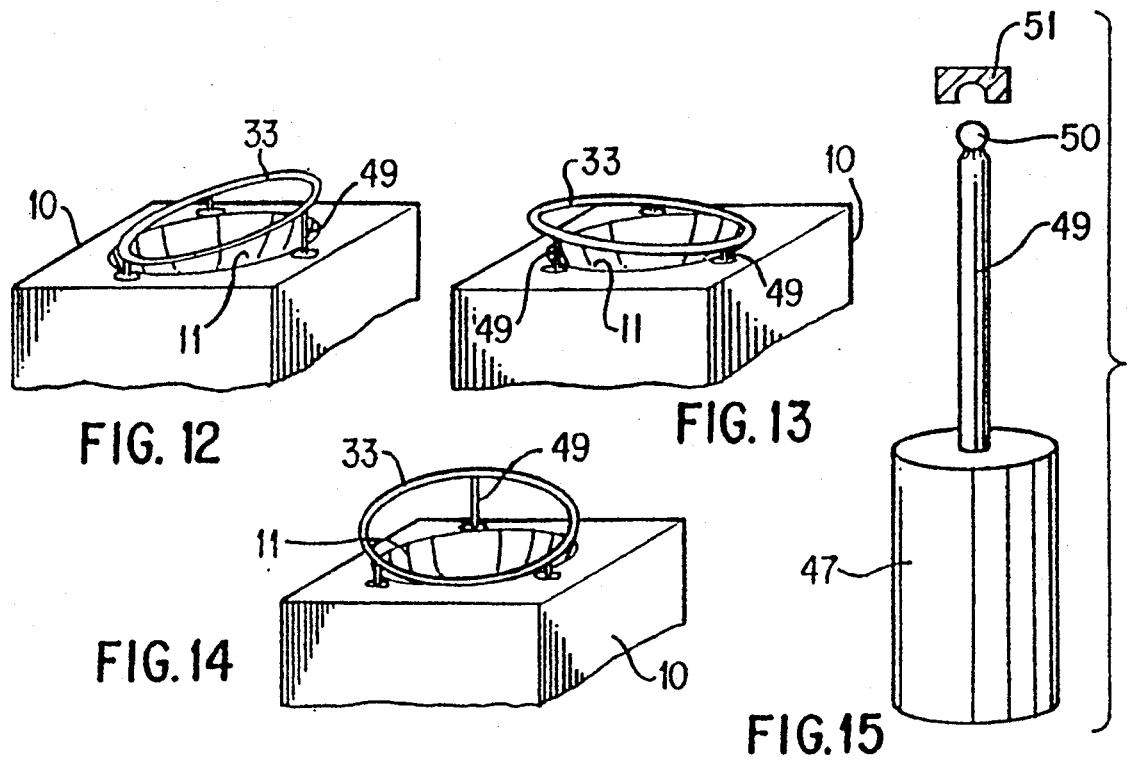
FIG. 12
FIG. 13
FIG. 14
FIG. 15

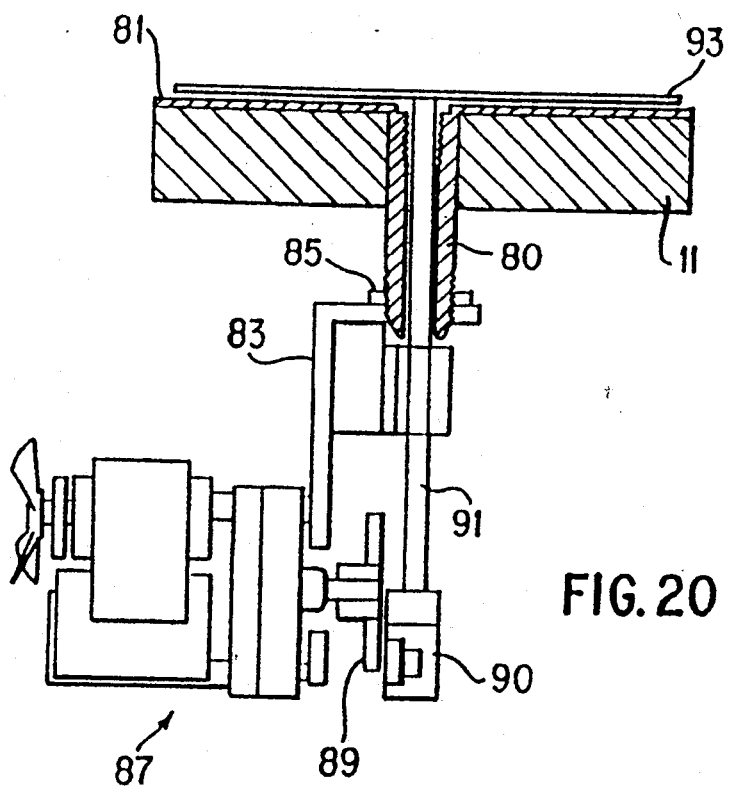
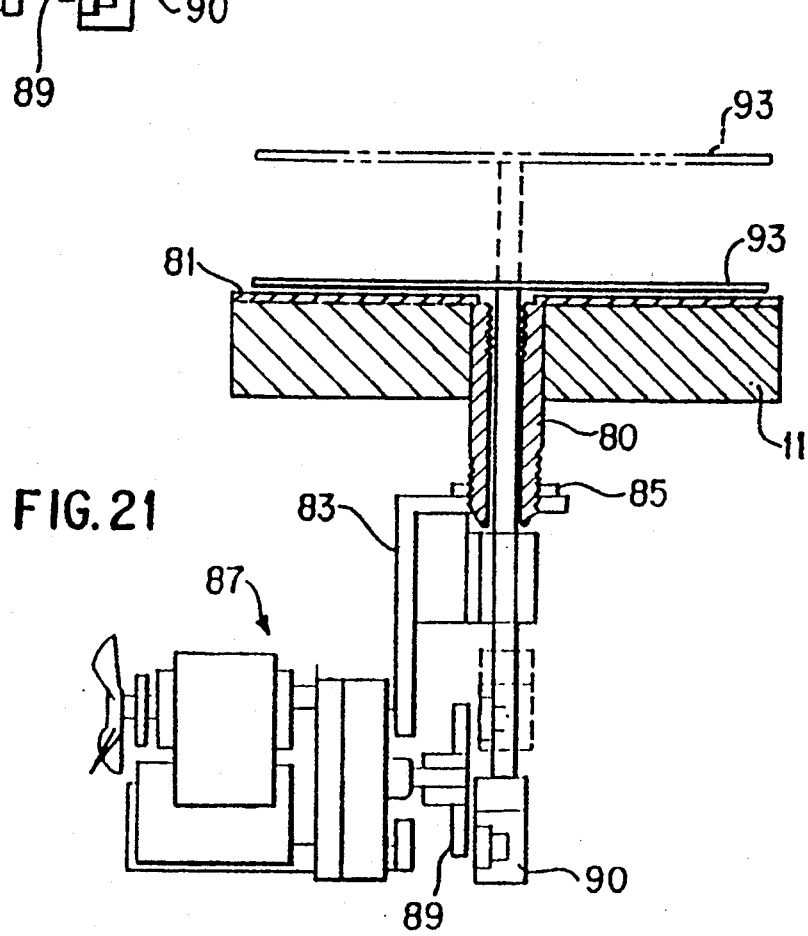

METHOD AND APPARATUS FOR FORMING AND COLLECTING SURGICAL SLUSH

This application is a division of Ser. No. 08/125,279, filed Sep. 23, 1993, now U.S. Pat. No. 5,331,820.

BACKGROUND OF THE INVENTION

1. Technical Field

The present invention pertains to improvements in methods and apparatus for producing and collecting surgical sterile slush. In particular, the invention is an improvement of the methods and apparatus disclosed in U.S. Pat. Nos. 4,393,659 (Keyes et al), 4,934,152 (Templeton) and 5,163,299 (Faries, Jr. et al). The disclosures in those patents are expressly incorporated herein in their entireties.

2. Discussion of the Prior Art

The above-referenced Keyes et al patent discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent, the Keyes et al system has a number of disadvantages. In particular, the separate product basin must be removed and re-sterilized after each use. Additionally, the glycol or other thermal transfer medium is highly flammable or toxic and, in any event, complicates the procedure. The Templeton patent discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al patent notes that scraping congealed liquid from the drape is undesirable in view of the potential for damage to the drape, resulting in a compromise of sterile conditions. As a solution to the problem, the patent proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel.

OBJECTS AND SUMMARY OF THE INVENTION

Accordingly, it is an object of the present invention to provide a method and apparatus for removing congealed liquid from the drape container in a surgical slush machine without endangering the integrity of the drape and thereby comprising the sterile conditions of the system.

It is another object of the present invention to provide a method and apparatus for automatically removing congealed liquid from a drape container in a surgical slush machine.

Another object of the present invention is to provide a method and apparatus for manipulating a sterile drape relative to the cooled basin walls in a surgical slush system, and doing so in a manner to dislodge solid pieces of a sterile medium adhering to the drape.

According to the present invention, sections of a sterile drape are pulled away from the supporting cooled basin wall of a surgical slush machine, thereby distancing congealed liquid (e.g., frozen pieces) formed on the drape interior from the cooled basin wall. The solid frozen pieces fall from the displaced drape portion and drop into the center of the drape container to collect as surgical slush. The drape sections may be successively lifted, pulled or manipulated by hand, but the preferred embodiment of the invention employs one of a variety of mechanisms for automatically manipulating the drape. In one embodiment the bottom of the drape is reciprocated up and down sufficiently to displace the sides of the drape container from the basin wall. In another embodiment the bottom of the drape container is repetitively twisted in opposite directions through a small angle to correspondingly twist the drape container sides away from the basin wall. In still another embodiment a wobble plate or disk continuously lifts portions of the drape container away from the basin wall. Yet another embodiment employs one or more rollers arranged to roll along the basin wall between the basin and the drape. A further embodiment includes a hoop or ring disposed on the top surface of the surgical slush machine about the basin periphery and movable manually or automatically to displace the drape container from the cooled basin wall.

The invention also includes providing a refrigerated compartment in the surgical slush machine to permit storage and pre-cooling of liquid for use in forming the sterile slush.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

BRIEF DESCRIPTION OF THE DRAWINGS

FIG. 4 is an elevational view in partial section of another embodiment of a mechanism of the present invention for manipulating the drape in a surgical slush machine.

FIGS. 5, 6, 7, 8, 9 and 10 are partially diagrammatic illustrations showing the manner in which the embodiment of FIG. 4 may be utilized to manipulate the drape in the surgical slush machine.

FIG. 11 is a top view in plan, partially diagrammatic, of another embodiment of a mechanism of the present invention for manipulating a sterile drape in a surgical slush machine.

FIGS. 12, 13 and 14 are partially diagrammatic views in prospective showing respective stages of operation of still another embodiment of the invention for manipulating a drape in a surgical slush machine.

FIG. 15 is a view in perspective of an actuator utilized in the embodiment of FIGS. 12-14.

FIGS. 20 and 21 are diagrammatic illustrations of still another mechanism of the invention for manipulating a sterile drape in a surgical slush machine, the two figures showing the mechanism during different portions of its sequence of operation.

DESCRIPTION OF THE PREFERRED EMBODIMENTS

Figure 1:
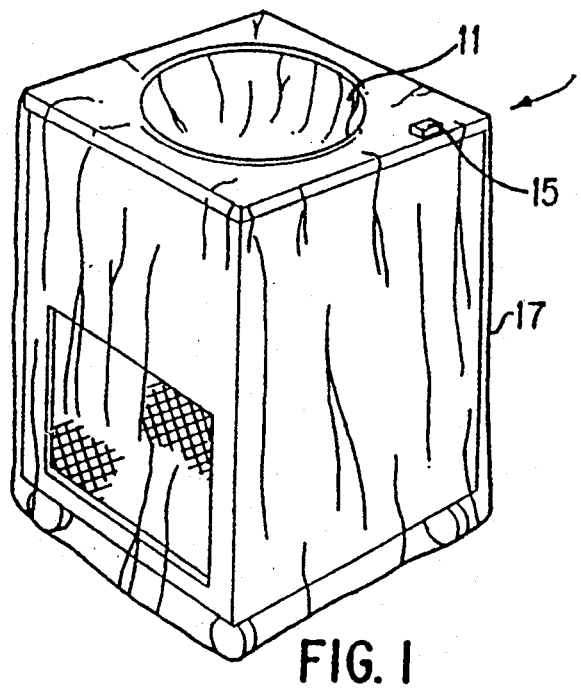
FIG. 1 is a view in perspective of a surgical slush machine of the type employed in the present invention.
Figure 3:
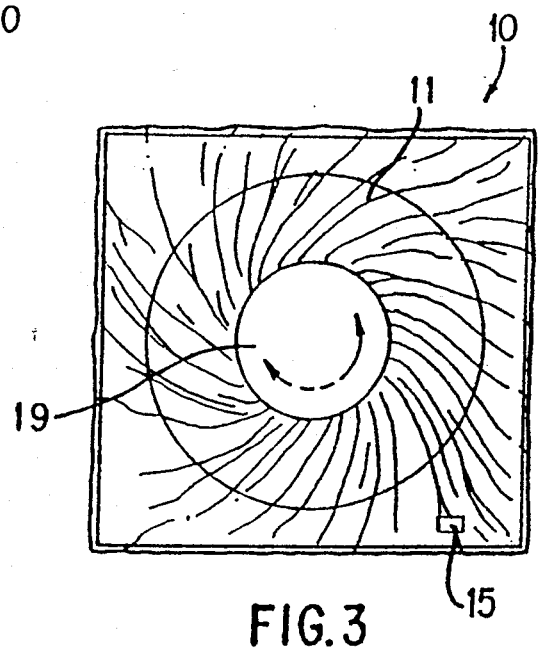
FIG. 3 is a top view in plan of the embodiment of FIG. 2.
Figure 2:
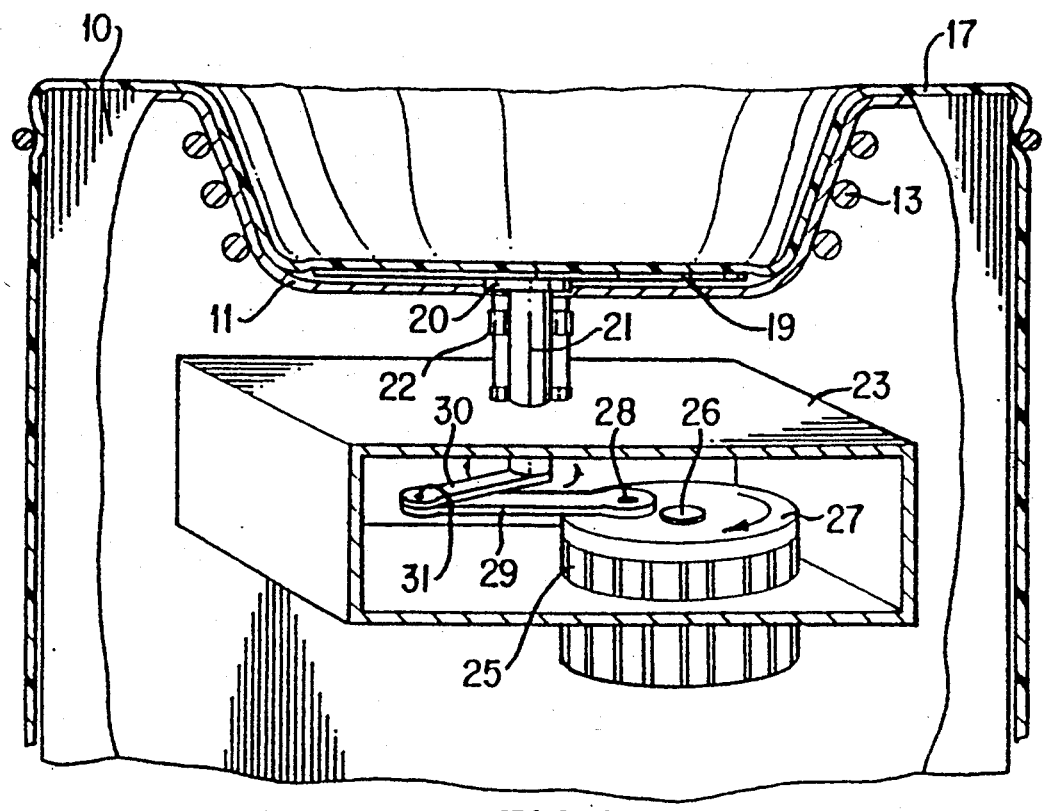
FIG. 2 is an elevational view in partial section showing one embodiment of a mechanism of the present invention for manipulating a sterile drape in a surgical slush machine.

Referring to FIGS. 1-3 of the accompanying drawings, a surgical slush generating system of the type described in the above-referenced Templeton patent includes a cabinet 10 with a top surface having a basin 11 mounted thereon in an appropriately sized recess. Basin 11 is made of thermally conductive material, typically stainless steel, and includes a generally flat bottom wall and a frusto-conical side wall. A conventional refrigeration unit is disposed within cabinet 10, it being noted that only the evaporator 13 of that unit is shown in FIG. 3. The refrigeration unit typically includes a compressor, a condenser and an expansion control unit connected by appropriate fluid conduits in a closed refrigeration loop with evaporator 13. The evaporator is in the form of a coil wound about the exterior surface of basin 11 in thermal transfer relation therewith. When the refrigeration unit is activated by means of appropriate controls 15, evaporator 13 cools the side wall of basin 11 to a temperature substantially below the freezing temperature of the liquid used in forming the sterile slush. This temperature is preferably on the order of $-30°$ F. to $10°$ F. For further details of the structure and operation of the refrigeration unit, reference is made to the aforementioned Keyes et al and Templeton et al patents.

A sterile drape 17, preferably transparent, is disposed over the top and sides of cabinet 10 and made to conform to the side wall and bottom of basin 11. The portion of drape 17 disposed in the basin serves as a sterile receptacle for sterile liquid placed therein to be frozen into the desired sterile slush. Typical sterile liquid used for this purpose is a 0.80% to 0.95% sodium chloride solution (i.e., saline). Drape 17 is made from a material that is impervious to the sterile liquid and sufficiently soft and flexible to conform to the basin wall. The drape may also have a preformed section contoured to match the contour of the basin. The thickness of the drape is preferably minimized to render thermal transfer therethrough most efficient, yet the thickness is sufficient to resist tearing and puncturing during normal use. Typically, by way of example only, the drape may be made of materials commonly used in hospitals for surgical drapes and has a thickness in the range of 3.0 to 10.0 mils. Drape 17 may also be made of polyurethane film as disclosed for the drape in the aforementioned Templeton patent. The drape is designed to be disposable after a single use and is provided pre-sterilized and pre-packaged in a manner to preserve its sterile state during storage.

When the surgical slush machine is operating, the sterile liquid in the drape container freezes in pieces on the side walls of that container. In order to dislodge these frozen pieces so as to form sterile slush within the drape container, a generally circular plate or disk 19 is disposed between the drape 17 and the bottom wall of basin 11. Disk 19 is horizontally oriented and substantially centered at the bottom of the basin, and the top surface of disk 19 is attached to the underside of drape 17. This attachment may be permanent or removable (e.g., by Velcro, or the like), so long as the bottom of the drape container rotates with the disk in the manner described below.

The center of the bottom surface of disk 19 has secured thereto a circular flange 20 disposed at the upper end of a rotatable shaft 21. The diameter of flange 20 is substantially smaller than the diameter of disk 19. Shaft 21 extends vertically downward from flange 20 through a suitably provided central hole in the bottom wall of basin 11 into a drive housing 23 located interiorly of cabinet 10. A suitable bearing assembly 22 is provided about shaft 21 between basin 11 and the drive housing 23. The drive motor 25, located at least partially within housing 23, is actuable to rotate a circular drive plate or crank 27 disposed horizontally within the drive housing. An idler arm 29 is pivotably joined to crank 27 at a pivot location 28 radially displaced from the center 26 of the crank. The idler arm extends horizontally beyond the crank periphery where its distal end pivotably engages one end of a horizontal agitator arm 30 at a pivot point 31. The opposite end of agitator arm 30 is fixedly secured to shaft 21 proximate the shaft bottom end.

As crank 27 is continuously rotated by motor 25 in one direction (e.g., in the direction of the arrow in FIG. 2), idler arm 29 is alternately pulled proximally and pushed distally, taking the pivotably joined end of agitator arm 30 with it. In so moving, the idler arm also pivots as necessary about pivot 28 to accommodate the restriction placed on transverse movement of the agitator arm by the latter being fixedly connected to shaft 21. As agitator arm 30 is pulled and pushed by the idler arm 29, it is caused to pivot back and forth through a small angle about the horizontal axis of shaft 21 to which the agitator arm is joined. Shaft 21, as a consequence, rotates back and forth through the same small angle. The angle of shaft rotation is typically between 1° (or less) and 90°.

As shaft 21 rotates in alternate directions it causes disk 19 to similarly rotate, and the attached drape bottom rotates therewith. The drape is thus rotatably twisted at its side walls in alternate directions relative to the basin side walls, this action being best illustrated in FIG. 3. As the drape side walls are displaced relative to the basin side walls, the solid pieces of frozen sterile medium dissociate from the drape side wall and fall into the central area of the drape container where slush is collected.

The embodiment described above is only one example of numerous ways in which a sterile drape container in a surgical slush machine can be agitated or manipulated to release frozen pieces of the sterile medium from the drape side wall. For example, in the embodiment illustrated in FIGS. 4, 5, 6 and 7 there is disclosed a hand manipulable hoop or ring 33 disposed horizontally on the top surface of cabinet 10 beneath the drape 17. The inside diameter of hoop 33 is greater than the outside diameter of the basin 11. Hoop 33 may be made of plastic, metal or other suitable material and is re-usable without sterilization since it is disposed beneath the sterile drape and does not come in to contact with the sterile slush. An annular clip 34 of generally semi-cylindrical cross-section resiliently snaps onto hoop 33 with the overlying drape portion trapped between the clip and hoop. In order to manipulate drape 17, a surgeon, nurse or aide grasps clip 34 and moves it and the hoop and trapped drape portions horizontally in the directions illustrated by arrows in FIGS. 5, 6 and 7. In particular, hoop 33 is slid transversely and rotated slightly in a generally eccentric motion relative to basin 11. Such motion causes the drape to be pulled upwardly along the side of the basin and to be rotatably twisted relative to the basin. As a consequence the adhering frozen pieces of sterile medium (e.g., saline) are displaced from the cooled basin side wall and fall from the drape. This method of manual manipulation is analogous to the manual manipulation method suggested in the aforementioned Faries, Jr. et al patent but is performed with an implement, in the form of hoop 33 and clip 34, to facilitate such manipulation. The person doing the manipulation moves the hoop as necessary to dislodge the adhering frozen pieces of sterile medium.

Alternatively, or in addition, hoop 33 may be lifted and taken out of plane in the manner illustrated in FIGS. 8, 9 and 10. As the hoop is lifted along with drape 17 at one side of the basin, that portion of the drape is displaced from the basin wall. The frozen pieces of the sterile medium that had been attached to the lifted portion of the drape fall into the interior portion of the drape container where the slush is collected.

In the embodiments of FIGS. 4–10 it is contemplated that hoop 33 be moved manually. It is also possible to move the hoop automatically. For example, referring to FIG. 11, hoop 33 may be retained in and horizontally reciprocated along two parallel tracks 35, 37 extending along opposite sides of basin 11. The tracks are secured to the top surface of cabinet 10 and are spaced by a distance substantially equal to the outside diameter of hoop 33. The configuration of the tracks permits the hoop to slide back and forth in the direction of the tracks. A drive motor, typically operated when the refrigeration loop is actuated by switch 15 (FIG. 1), includes a horizontally oriented crank wheel 39 rotatable about the motor axis 40. An idler arm 41 has a proximal end pivotally secured to the crank wheel at a location radially spaced from axis 40. The distal end of idler arm 41 terminates in a ball member 43 engaged by a socket member 45 secured to hoop 33, thereby forming a ball joint. Upon rotation of crank wheel 30 by its motor, idler arm 41 is alternately pulled proximally and pushed distally to thereby reciprocate hoop 33 proximally and distally of motor axis 40 along the top surface of the cabinet. Although drape 17 is not illustrated in FIG. 11 in order to preserve clarity and understanding of the manipulating mechanism, it will be understood that hoop 33, when thusly reciprocated, pulls on the drape to displace it from the cooled side wall of the basin 11. As a consequence, frozen saline pieces are dislodged from the drape and collect in the drape receptacle as sterile slush.

A mechanism for alternately effecting out of plane tilting of hoop 33 is illustrated in FIGS. 12–15. In particular, a plurality of solenoids 47 is disposed at equiangular spaced locations about basin 11. Each solenoid includes a normally retracted rod 49 that is extended in a longitudinal direction when the solenoid is energized. The bodies of solenoids 47 are disposed beneath the top surface of cabinet 10, and suitable apertures are provided through that top surface to permit rods 49 to be selectively extended upwardly beyond the surface.

At the distal end of each rod 49 is a ball 50 adapted to be received and engaged in a respective socket member 51 secured to the underside of hoop 33. In the illustrated embodiment there are three solenoids 47 located at 120°-spaced locations about the basin. Similarly, the downwardly facing side of hoop 33 has three sockets 51 secured thereto and located at 120°-spaced locations. It will be appreciated that as each solenoid is individually actuated, either by individual manually actuated switches or by an automatic sequencer, its rod 49 is extended upwardly and pushes a portion of the hoop upwardly to cause the hoop to tilt. Sequential actuation of individual solenoids 47 causes the hoop to be raised at successive locations. The drape (not illustrated to preserve clarity in FIGS. 12–14) is similarly raised with the hoop to displace the drape from the cooled basin side wall. As a consequence, frozen pieces of sterile medium fall from the drape and collect as surgical slush in the drape receptacle. In order to avoid inadvertently pulling the drape and dislodging it from its mounted position on cabinet 10, a band 63 is provided to circumscribe the sides of the cabinet and securely retain the drape 17 between the cabinet and band at a location near the top of the cabinet.

Figure 16:
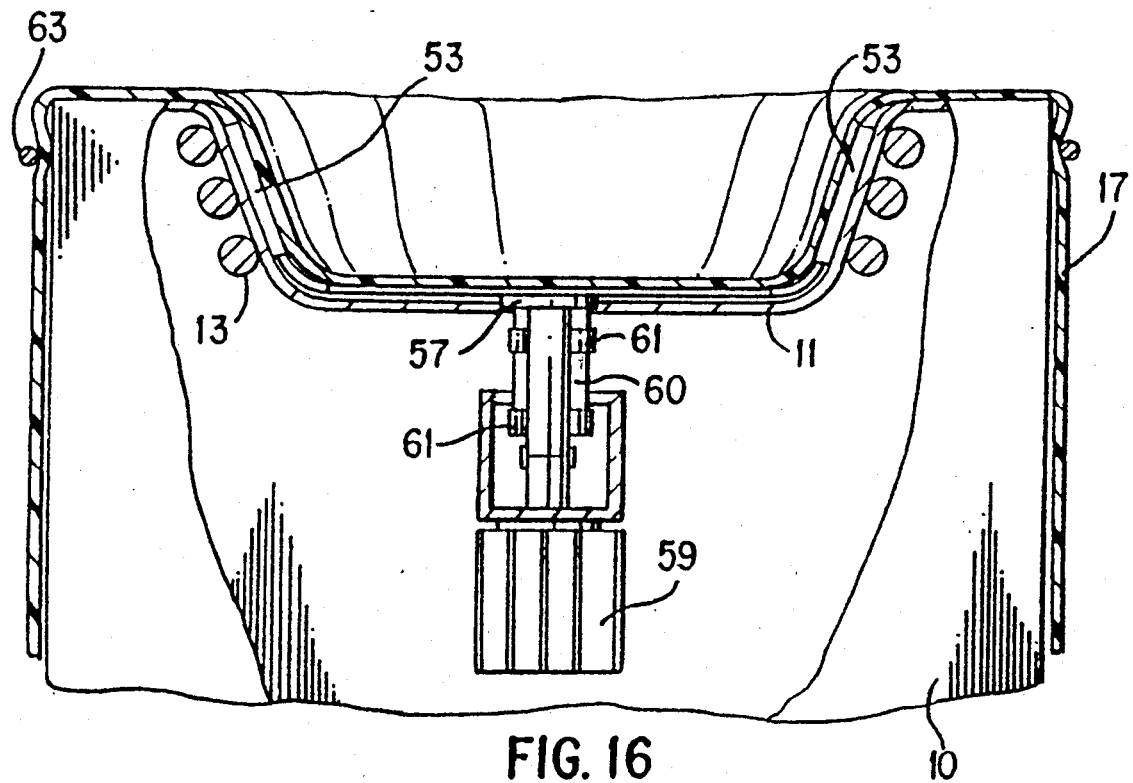
FIG. 16 is an elevational view in partial section showing another embodiment of a mechanism of the invention for manipulating a sterile drape in a surgical slush machine.
Figure 17:
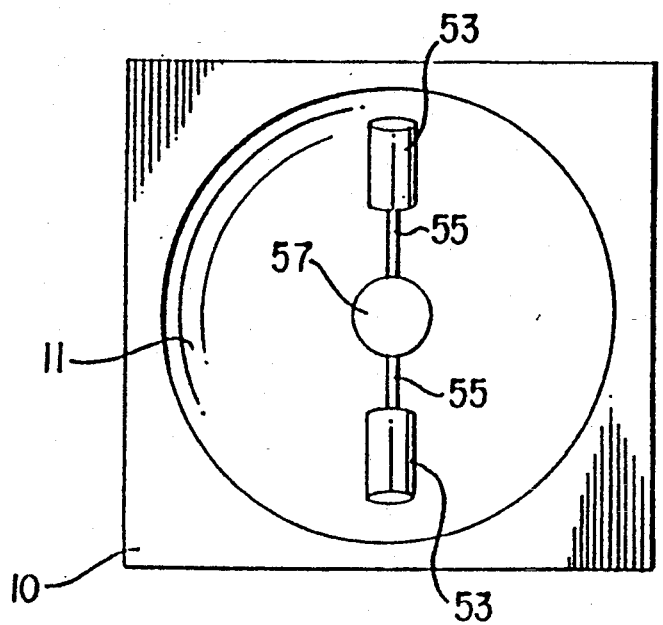
FIG. 17 is a top view in plan of the mechanism illustrated in FIG. 16.

Another method and apparatus for manipulating the drape is illustrated in FIGS. 16 and 17. In this embodiment the manipulation of the drape is effected by a plurality of elongated rollers 53 adapted to roll along the interior side wall of basin 11 between the basin and drape 17. Each roller 53 is a hollow cylinder mounted for rotation on and about a respective rod 55. Rods 55 have proximal ends joined to and radially extending from a rotatable disk 57 disposed at the center of the bottom of basin 11 between the basin and drape 17. Each rod is bent to form a section extending generally upward along the diverging side wall of the basin. It is that rod section about which roller 53 is rotatably secured. Preferably, rods 55 have sufficient resilience to urge rollers 53 outwardly against the basin wall 17. Continuous slow rotation of disk 57 (e.g., one to five revolutions per minute) thus causes the rollers to move between the drape and basin to displace the drape from the cooled basin side wall. Frozen pieces of the sterile medium are thus removed from the source of colder temperature and fall into the collected pile of sterile slush.

It should be understood that, instead of rollers 53, other shapes of separating members may be provided on arms 55 to displace the drape 17 from the basin side wall as the arms 55 rotate along the wall. For example, wedges, fins, etc. may be utilized for this purpose.

Figure 18:
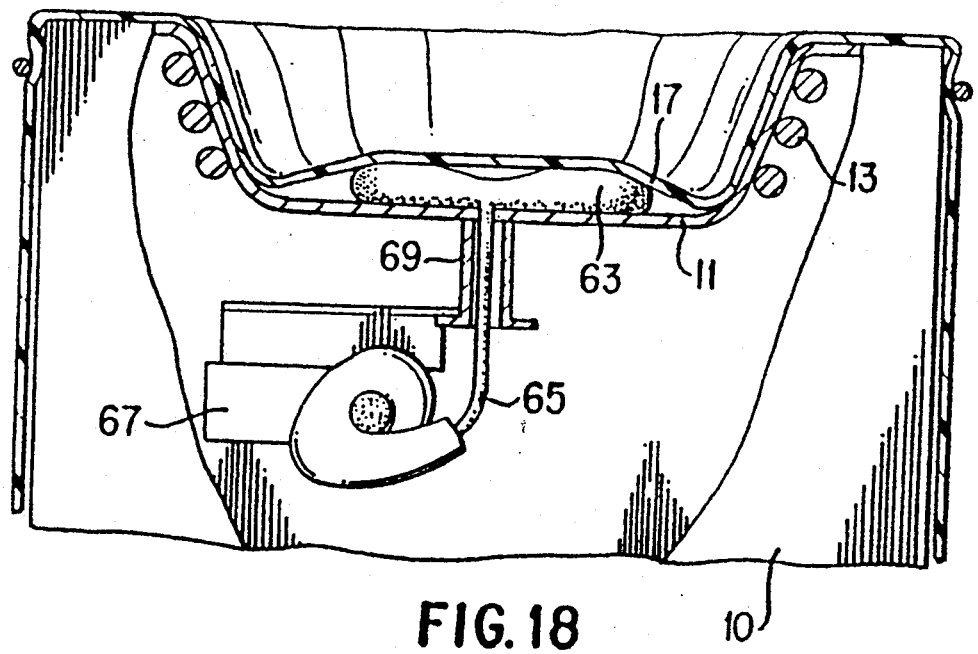
FIG. 18 is an elevational view in partial section of still another embodiment of a mechanism of the invention for manipulating a sterile drape in a surgical slush machine.

Still another embodiment of the invention is illustrated in FIG. 18 wherein an inflatable bladder 63 is illustrated disposed at the bottom of basin 11 between the basin bottom wall and drape 17. An inflation tube 65, preferably formed integrally with the bladder, extends downwardly through a suitably provided opening or hole in the bottom of the basin to a pump 67 mounted within cabinet 10. Pump 67 may be supported, for example, by means of a guide cylinder 69 mounted vertically with its upper end secured to the bottom of basin 11 in coaxial relation with the access hole for inflation tube 65. Inflation tube 65 extends through the guide cylinder 69 to pump 67, the latter being mounted on and suspended from the bottom end of the guide cylinder.

Figure 19:
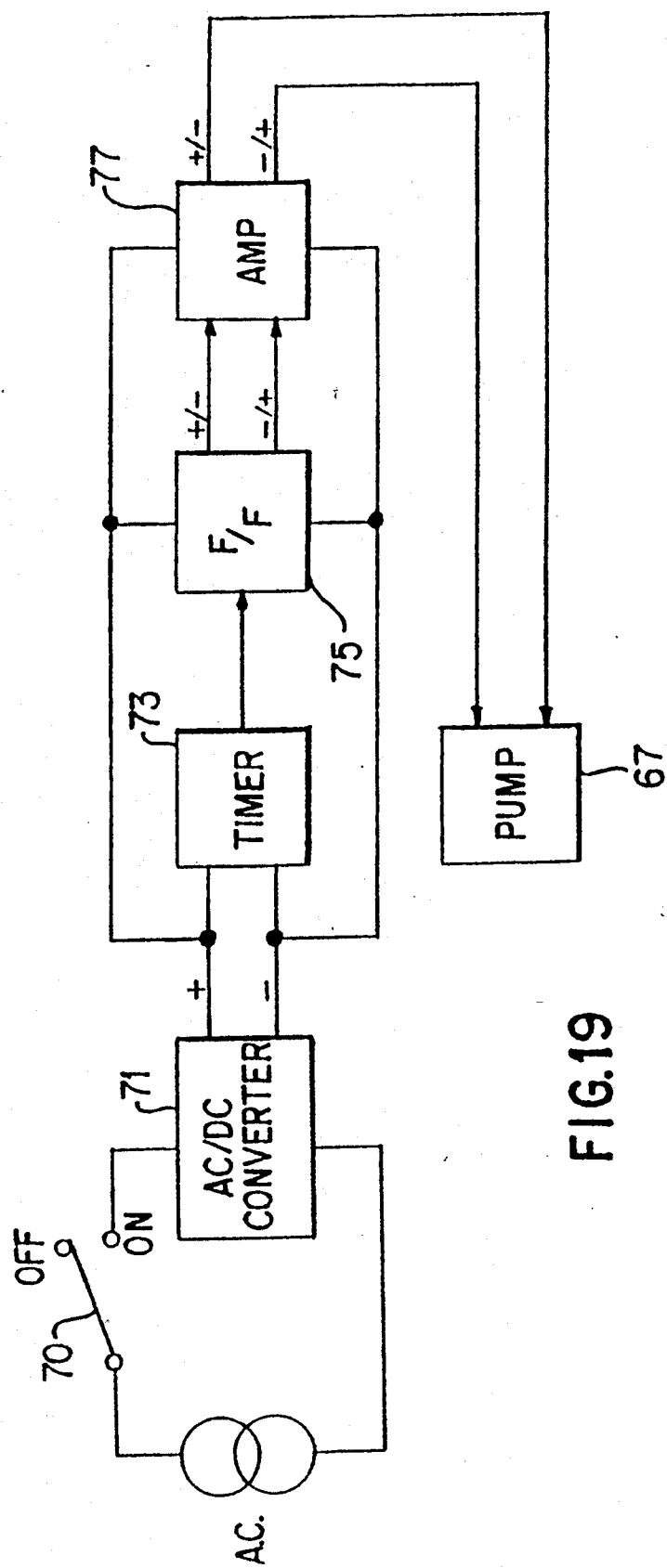
FIG. 19 is an electrical schematic diagram of a circuit for energizing the pump employed in the embodiment of FIGS. 16 and 17.

Pump 67 is of a type which is operable to provide either positive pressure or aspiration (i.e., negative pressure) at inflation tube 65, depending upon the polarity of the voltage applied to the pump supply terminals. Referring to FIG. 19, there is illustrated an example of an electrical circuit for continuously alternating the pump operation mode between pressurization and aspiration. Specifically, primary a.c. voltage is applied to an AC/DC converter 71 when a switch 70 is closed. Switch 70 may be actuated, for example, when the refrigeration power switch 15 (FIG. 1) is actuated. The d.c. voltage from converter 71 is applied to a timer 73 arranged to continuously cycle to provide a series of output pulses at regular timed intervals (e.g., every five to thirty seconds). That output signal clocks a flip-flop 75 of the type that responds to each pulse by changing the polarity of the voltage at its output signal lines. Those output signal lines are connected to a driver amplifier 77 arranged to amplify the alternating polarity voltages and alternately drive pump 67 between its two operating modes.

It will be appreciated that there are multiple ways of manipulating drape 17 to achieve the desired separation of frozen saline from the drape and thereby cause the frozen pieces to collect as sterile surgical slush. For example a pump such as pump 67 may be operated without a bladder to alternately pressurize and aspirate space between the drape and the basin. If desired, the basin walls may be contoured to provide flow passages from the bottom of the basin up along the sidewall to assist in separating the drape receptacle sides from the basin sidewall. Alternatively, the pressurized air may be delivered directly through suitably provided holes in the basin sidewall to alternately produce air bubbles between the basin sidewall and adjacent portions of the drape.

Another mechanism for manipulating the drape receptacle is illustrated in FIGS. 20 and 21 to which specific reference is now made. It is to be understood that, in FIGS. 20 and 21 and in other drawings described below, the drape and cabinet are omitted for the purpose of avoiding repetition and to promote a clear understanding of the mechanism illustrated in those drawings. In FIGS. 20 and 21 the bottom of basin 11 is provided with a central hole through which an adapter tube 80 extends. Adapted tube 80 has an annular flange 81 extending radially outward from the upper end of the tube and positioned to rest on the bottom wall of the basin between the basin and the drape container (not shown). The bottom end of adapter tube 80 is externally threaded and is engaged by a support bracket 83 and lock washer 85 such that bracket 83 is suspended interiorly of the machine cabinet (not shown). A gear motor assembly, generally designated at 87, is supported by bracket 83 and includes a rotor 89 operatively engaged with a bearing track 90. A drive shaft 91 has its bottom end operatively engaged to bearing track 90 to cause the shaft to reciprocate longitudinally as rotor 89 rotates. Shaft 91 extends upwardly through adapter tube 80 and has its upper end secured to the center of the underside of a plate 93 disposed between the adapter tube flange 81 and the bottom of the drape receptacle (not shown). Accordingly, as motor 87 reciprocates shaft 91 up and down, the shaft moves plate 93 up and down. The plate, in turn, moves the bottom of the drape container up and down to loosen attached pieces of frozen saline.

Figure 22:
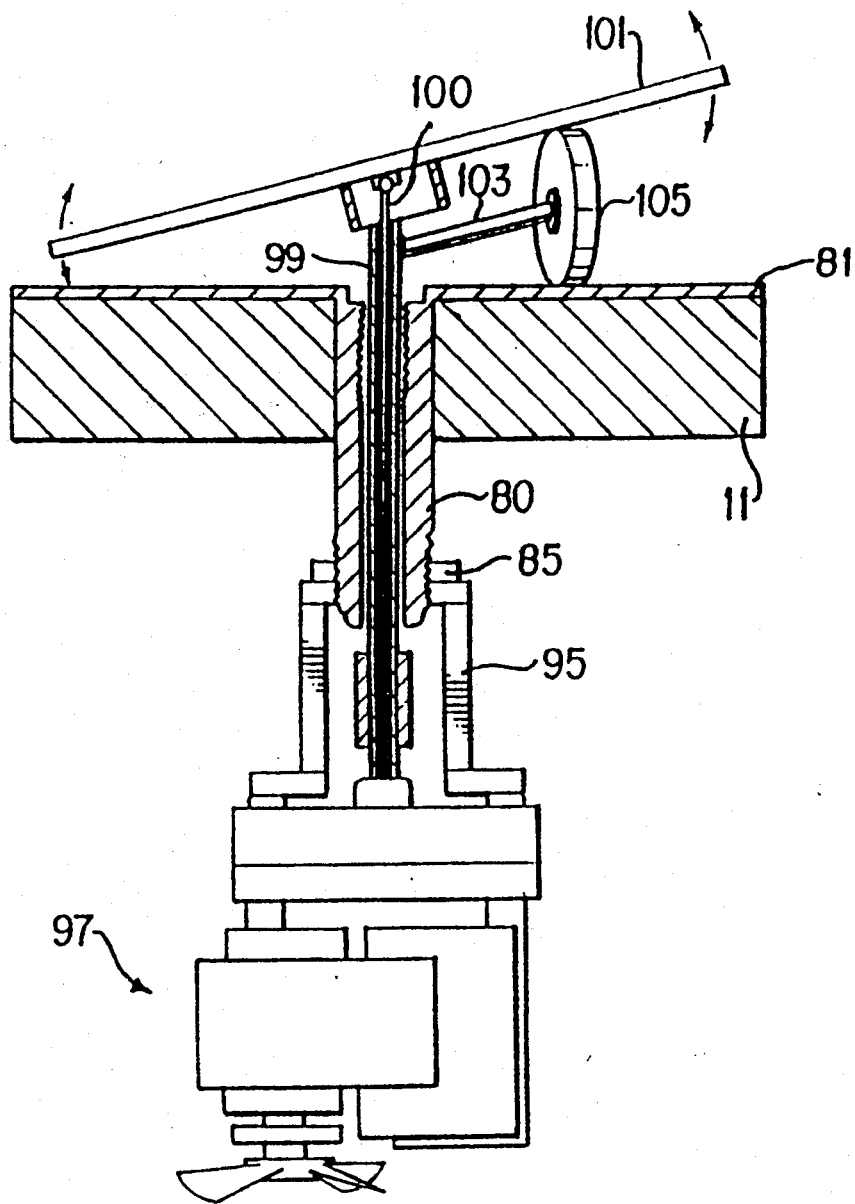
FIG. 22 is a partially diagrammatic illustration of another mechanism of the invention for manipulating a sterile drape in a surgical slush machine.

Referring next to FIG. 22 another embodiment of the invention utilizes a wobble plate technique for dislodging frozen pieces of saline. Specifically, as with the embodiment described immediately above, adapter tube 80 includes an annular flange 81 resting on the bottom of basin 11. The adapter tube includes an externally threaded bottom end engaged by a bracket 95 and a lock washer 85. Bracket 95 supports a gear motor assembly 97 within the machine cabinet and has a hollow vertical drive shaft 99 that rotates about its own longitudinal axis when driven by the motor. Drive shaft 99 extends upwardly through the adapter tube 80 to a location above flange 81. A rigid rod 100 extends vertically upward through hollow drive shaft 99 to a height above the drive shaft, and terminates in a ball member at the upper end of the rod. Rod 100 is mounted to motor 97 in a manner such that the rod does not rotate with drive shaft 99. A wobble plate or disk 101 has a socket centrally located on its underside for receiving the ball on rod 100 to thereby freely permit tilting of the disc about the ball joint. Proximate the upper end of drive shaft 99 there is secured a connecting shaft 103 extending generally transversely from the drive shaft. The distal end of connecting shaft 103 is journaled at the center of a wheel or roller oriented to roll along flange 81. As drive shaft 99 rotates about its own axis it causes shaft 103 to revolve about that axis with wheel 105. The wheel thus rolls in a circular path about the drive shaft axis. The diameter of wheel 105 is chosen to be larger than the spacing between disc 101 and flange 81 when the disc is oriented parallel to the flange. Accordingly, as the wheel rolls orbitally about the drive shaft axis, the wheel forces the adjacent portion of disc 101 upward, thereby forcing the diametrically opposite end of the disc downward as the disc pivots about the ball joint. Disc 101 thus wobbles about the drive shaft axis under the impetus of the revolving wheel. A drape container (not shown) resting on disc 101 has successive portions lifted and displaced from the basin as the disc 101 wobbles, thereby causing frozen saline pieces to dislodge from the drape.

Figure 23:
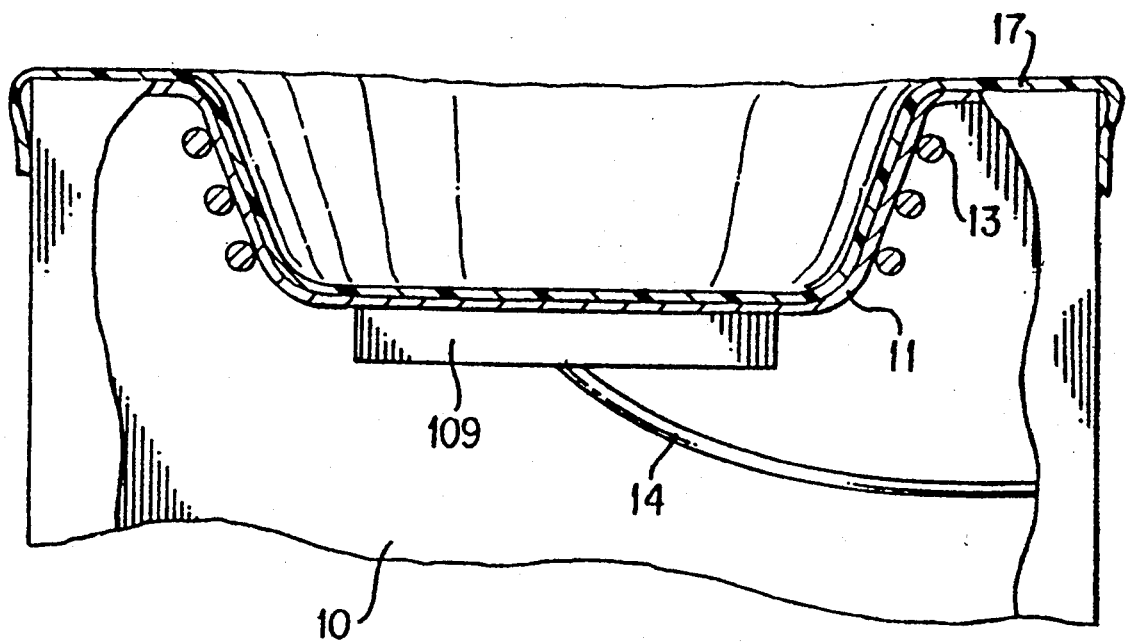
FIG. 23 is an elevational view in partial section of still another mechanism of the invention for manipulating the sterile drape in a surgical slush machine.

Another embodiment of the invention utilizes vibrations to manipulate the drape and dislodge frozen saline. Referring to FIG. 23, a vibrator 109 is secured by adhesive, or the like, to the bottom of basin 11 and is energized by primary a.c. voltage via cable 111 when the system power is turned on. Vibrator 109 is preferably an ultrasonic vibrator and functions to transmit vibrations through the wall of basin 11 to the drape receptacle contoured to the basin. The vibrations cause the frozen saline to dislodge from the drape and collect as slush.

It will be appreciated that the embodiments described above and illustrated in the drawings represent only a few of the many ways of achieving drape manipulation for the purpose of dislodging frozen pieces of sterile medium in a surgical slush machine.

Figure 24:
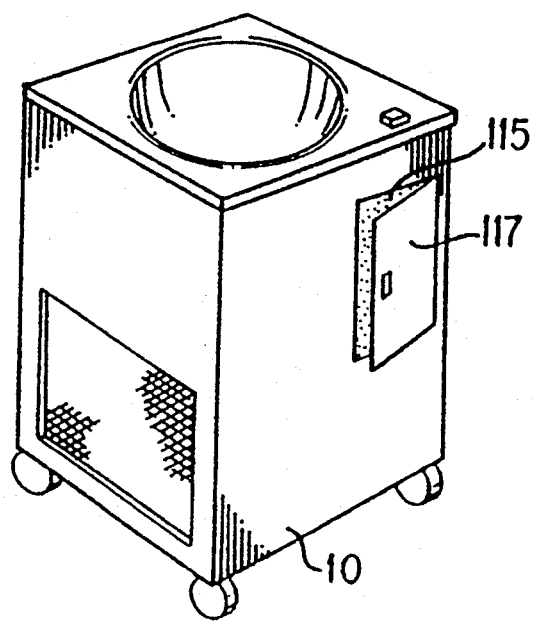
FIG. 24 is a view in perspective of a surgical slush machine showing a storage compartment according to the invention for pre-chilling sterile saline or similar medium.
Figure 25:
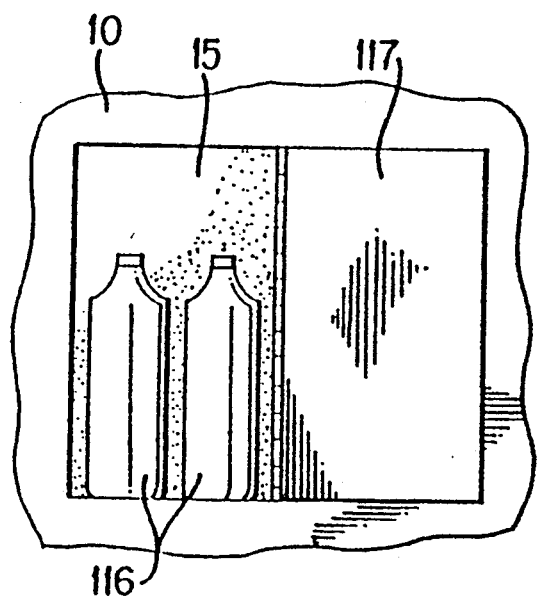
FIG. 25 is a detailed view in elevation of the storage compartment of FIG. 24.

In order to reduce the time required for saline or other sterile medium to freeze in the drape container, it is desirable to pre-chill the saline before it is poured into the container. It is often inconvenient to keep a separate refrigerator for the saline near the operating table in the surgical theater. In accordance with another aspect of the present invention, and referring now to FIGS. 24 and 25, the surgical slush machine of the present invention includes a refrigerated compartment 115 defined in one side of cabinet 10. A compartment door 117 provides closure for and access to compartment 115, and a plurality of bottles 116 of saline solution may be stored and pre-chilled within the compartment. Compartment 115 may be refrigerated by a separate evaporator connected in parallel with evaporator 13 in a common refrigeration loop. Alternatively, a separate refrigeration loop may be provided for the additional evaporator. In either case the evaporator is in contact with the walls of the compartment 115 inside cabinet 10 to cool the compartment interior and permits pre-chilling of the saline bottles 116.

From the foregoing description it will be appreciated that the invention makes available a novel surgical slush system and a method for forming surgical slush wherein a sterile drape container is manipulable, by any of a variety of different techniques, to dislodge frozen sterile medium from the drape to permit efficient collection of slush in the center of the drape container. In addition, the invention makes available a convenient method and apparatus for pre-chilling sterile liquid medium for use in the surgical slush machine.

Having described preferred embodiments of a new and improved method and apparatus for forming and collecting surgical slush, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. Apparatus for forming sterile surgical slush comprising:
   a cabinet housing the apparatus;
   a basin disposed in said cabinet;
   a refrigeration system for cooling said basin;
   a sterile drape overlying said apparatus and conforming to said basin to define a drape container for receiving sterile liquid to be converted to slush;
   wherein said refrigeration system cools the basin sufficiently to freeze the sterile liquid therein and cause pieces of the frozen liquid to adhere to the drape container; and
   manipulation means for automatically manipulating said drape relative to said basin to dislodge the frozen pieces from the drape.

2. The apparatus of claim 1 wherein said manipulation means includes:
   a movable member disposed between said drape and said cabinet; and
   drive means for continuously moving said movable member to displace successive portions of said drape from said basin.

3. The apparatus of claim 2 wherein said drive means includes means for repetitively moving said movable member back and forth in opposite directions.

4. The apparatus of claim 1 wherein said manipulation means includes means for issuing pressurized fluid between said drape and said basin.

5. The apparatus of claim 1 further comprising a refrigerated compartment in said cabinet for storing and pre-chilling containers of said sterile liquid.

6. The apparatus of claim 1 wherein said manipulation means comprises means for lifting the bottom of the drape container sufficiently far away from the bottom of the basin to displace at least portions of the sides of the drape container from the cooled basin.

7. The apparatus of claim 6 wherein said manipulation means includes a plate disposed between said drape container and the bottom of the basin, and means for automatically and repetitively raising and lowering said plate.

8. The apparatus of claim 6 wherein said manipulation means includes a bladder disposed between the drape container and the basin, and means for automatically and repetitively inflating and deflating said bladder.

9. The apparatus of claim 1 wherein said manipulation means includes means for rotationally twisting the drape container relative to the basin.

10. The apparatus of claim 1 wherein said manipulation means includes at least one separation member movable along the sides of the basin between the basin and drape container, and means for moving said separation member to separate portions of the drape container from the basin.

11. The apparatus of claim 10 wherein said manipulation means includes means for rolling said separation member along the basin.

12. The apparatus of claim 1 wherein said manipulation means includes a plate disposed between the drape container and the basin, and means for automatically and continuously wobbling said plate to periodically displace different locations of the drape from the basin.

13. The apparatus of claim 1 wherein said manipulation means includes means for automatically and periodically delivering pressurized air to and exhausting pressurized air from between the drape container and the basin.

14. The apparatus of claim 1 wherein said manipulation means includes a member disposed on the top surface of said cabinet adjacent said basin and beneath said drape, and means for automatically moving said member to cause said drape to move relative to said basin.

15. The apparatus of claim 14 wherein said means for moving includes means for automatically sliding said member along said top surface.

16. The apparatus of claim 1 wherein said manipulation means includes means for automatically and repetitively raising and lowering successive portions of said drape relative to said basin.

17. The apparatus of claim 1 wherein said manipulation means includes means for imparting vibrations to the basin and drape container.

18. The apparatus of claim 1 wherein said manipulation means includes means for repetitively and sequentially separating plural portions of said drape from the sides of said basin.

19. The apparatus of claim 18 wherein said means for sequentially separating includes:
a generally annular member disposed beneath said drape; and
means for raising and lowering said annular member from different locations sequentially to tilt the annular member in changing angular orientations and displace the drape from the sides of said basin.

20. The apparatus of claim 18 wherein said means for sequentially separating includes:
a generally annular member disposed between said drape and said basin; and
means for raising and lowering said annular member from different locations in sequence to tilt the annular member in changing angular orientations and displace the drape from the sides of said basin.

21. In a surgical slush machine of the type wherein a sterile medium in liquid form is contained in a liquid-impervious sterile drape container conformed to a basin being cooled to cause the sterile medium to freeze and adhere to the drape adjacent the cooled portions of the basin, apparatus for detaching frozen pieces of the sterile medium from the drape, said apparatus comprising:
manipulation means for automatically and repetitively manipulating the drape relative to the basin to displace said drape from the cooled portions of the basin; and
wherein said drape container is positioned to collect said detached pieces as sterile slush.

22. The apparatus of claim 21 wherein said manipulation means comprises means for lifting a part of the drape container sufficiently far away from the basin to displace at least portions of the drape container from the cooled portions of the basin.

23. The apparatus of claim 22 wherein said means for lifting includes a member disposed between said drape container and the bottom of the basin, and means for repetitively and mechanically raising and lowering said member.

24. The apparatus of claim 22 wherein said means for lifting includes a member disposed beneath said drape container, and means for repetitively and mechanically raising and lowering said member.

25. The apparatus of claim 21 wherein said manipulation means includes means for repetitively and sequentially separating plural portions of said drape from the sides of said basin.

26. The apparatus of claim 25 wherein said means for sequentially separating includes:
a generally annular member disposed beneath said drape; and
means for raising and lowering said annular member from different locations in sequence to tilt the annular member in changing angular orientations and displace the drape from the sides of the basin.

27. The apparatus of claim 25 wherein said means for sequentially separating includes:
a generally annular member disposed between said drape and said basin; and
means for raising and lowering said annular member from different locations in sequence to tilt the annular member in changing angular orientations and displace the drape from the sides of the basin.

* * * * *